(12) United States Patent
Koyanagi

(10) Patent No.: US 7,540,660 B2
(45) Date of Patent: Jun. 2, 2009

(54) MEDICAL IMAGING APPARATUS

(75) Inventor: Takahiro Koyanagi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/184,305

(22) Filed: Aug. 1, 2008

(65) Prior Publication Data

US 2009/0040333 A1    Feb. 12, 2009

(30) Foreign Application Priority Data

Aug. 9, 2007    (JP) .............................. 2007-207881

(51) Int. Cl.
*H01J 31/50* (2006.01)
(52) U.S. Cl. ...................................... 378/189; 378/197
(58) Field of Classification Search ................ 378/98.8, 378/189, 193–198
See application file for complete search history.

(56) References Cited

FOREIGN PATENT DOCUMENTS

| JP | 03-49687 U | 5/1991 |
|---|---|---|
| JP | 6-169904 | 6/1994 |
| JP | 2005-470 | 1/2005 |

*Primary Examiner*—Courtney Thomas
(74) *Attorney, Agent, or Firm*—Fitzpatrick, Cella, Harper & Scinto

(57) ABSTRACT

When a safety switch is ON in step S1, and a movement lock portion and a safety lock portion are locked in step S2, a movement lock switch becomes inoperable and a detachment/attachment lock release button becomes operable. When a detachment/attachment lock portion is released in step S3, an imaging portion becomes attachable or detachable in step S4a or S4b. If the imaging portion is present, a type detecting unit discriminates its type in step S7. Adjustment is performed so that a weight is balanced with a total weight of the discriminated imaging portion and the holder in step S8.

4 Claims, 6 Drawing Sheets

MEDICAL IMAGING APPARATUS

BACKGROUND OF THE INVENTION

1. Field of the Invention

The present invention relates to a medical imaging apparatus in which an imaging portion is movable to a position of a subject by way of a weight balance mechanism.

2. Description of the Related Art

An imaging apparatus in which an imaging portion is vertically movably supported so that it can be arranged in a desired posture typically employs a manual movement mechanism to keep a weight balance using a mechanism which couples the imaging portion with a weight having an equivalent weight to that of the imaging portion by a wire or the like, or that uses a balance control mechanism with a spring force. Such an imaging apparatus that employs the weight balance mechanism is applied to, for example, a radiographic imaging apparatus supported with a vertical stand or a C-arm.

FIG. 6 shows a supporting base of a typical radiographic imaging apparatus. A column 2 is vertically provided on a pedestal 1. A pulley 4 with a wire 3 wounded thereon is hung from an upper portion of the column 2. A first end of the wire 3 is connected to a weight 5, and a second end thereof is connected to a holder 7 that fixes an imaging portion 6. When a handle 8 provided in a side surface of the holder 7 is manually operated, the imaging portion 6 is vertically moved in a Z1 direction along the column 2 via the holder 7. The weight 5 has a weight which is balanced with the total weight of the imaging portion 6 and the holder 7. The weight 5 is vertically movable in a Z2 direction while the weight balance is constantly kept in the column 2.

Japanese Patent Laid-Open No. 6-169904 discloses an adjustment mechanism for a weight balance during rotational movement of a C-arm. In the mechanism, an imaging portion is coupled with a weight having an equivalent weight to that of the imaging portion to hold the weight balance. In recent years, with a progress in semiconductor process technology, an apparatus for imaging a radiographic image with a semiconductor sensor has been developed. FIG. 7 is a conceptual diagram showing an imaging system that uses such a radiographic imaging apparatus. A radiographic imaging apparatus 11 includes therein a radiation sensor 12. A subject S is irradiated with radiation emitted from a radiation source 13 arranged behind the subject S. The radiation transmitted through the subject S is converted into visible light through a fluorescent member provided in the radiation sensor 12. The visible light converted through the fluorescent member is detected as an electric signal by photoelectric conversion elements arrayed in a two-dimensional grid form.

A controller 14 that controls the radiation sensor 12 for driving of reading and image transferring is connected to the radiographic imaging apparatus 11. The controller 14 performs image processing for an image output from the radiation sensor 12, and displays a radiographic image of the subject S on a monitor 15.

In this imaging system, an image can be observed instantly, unlike a radiographic image recording and reproducing system that reads an image in post processing. Further, in this imaging system, a detection panel is provided on a dedicated pedestal corresponding to a capturing mode such as standing, lying, or the like. The detection panel is selected according to what is needed.

Recently, a portable X-ray detector has been developed and used for capturing an image with the subject in a desired capturing posture. Japanese Patent Laid-Open No. 2005-470 suggests an X-ray imaging apparatus in which such a portable X-ray detector is used, the X-ray detector is fixed at a position facing an X-ray tube, and the X-ray detector is used in a manner separated from a supporting portion.

With the portable X-ray detector, positioning can be easily performed, and alignment with high precision can be rapidly performed. Also, since the X-ray detector is arranged at a desired position, an image can be captured by moving the apparatus in accordance with the position of a subject, which is not movable, to reduce the burden on the subject. That is, two capturing modes can be provided with a single apparatus. This increases convenience of use.

Hitherto, in such an imaging apparatus, an imaging portion is disposed on a dedicated supporting device corresponding to a capturing mode. However, in recent years, there have been provided an apparatus in which a portable imaging portion is used, and a single supporting device is commonly used for a plurality of such imaging portions; or an apparatus in which an imaging portion has to be detached or attached during installation or the like. Hence, a weight balance may be disrupted when the imaging portion is detached or attached. If the weight balance is disrupted, the posture of the imaging portion may be rapidly changed, and inhibition operations relating to a detachment or attachment position and a condition of a movable portion have to be manually performed.

SUMMARY OF THE INVENTION

The present invention provides a medical imaging apparatus that overcomes the above disadvantages, that reduces a possibility of a rapid change in a posture of the medical imaging apparatus when a weight balance is disrupted, and that allows the imaging portion to be easily detached from or attached to the medical imaging apparatus.

A medical imaging apparatus according to an aspect of the present invention includes an imaging unit configured to detect or capture a two-dimensional image of a subject; a holding unit configured to detachably hold the imaging unit; a moving unit configured to change a position of the imaging unit manually; a balance control unit configured to keep a weight balance when the imaging unit is moved; a fixing unit configured to inhibit the moving unit from being operated; and a detachment/attachment inhibiting unit configured to inhibit the imaging unit from being detached when the fixing unit is being unlocked.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Preferred embodiments of the present invention will now be described in detail in accordance with FIGS. 1 to 5.

First Embodiment

Figure 1:
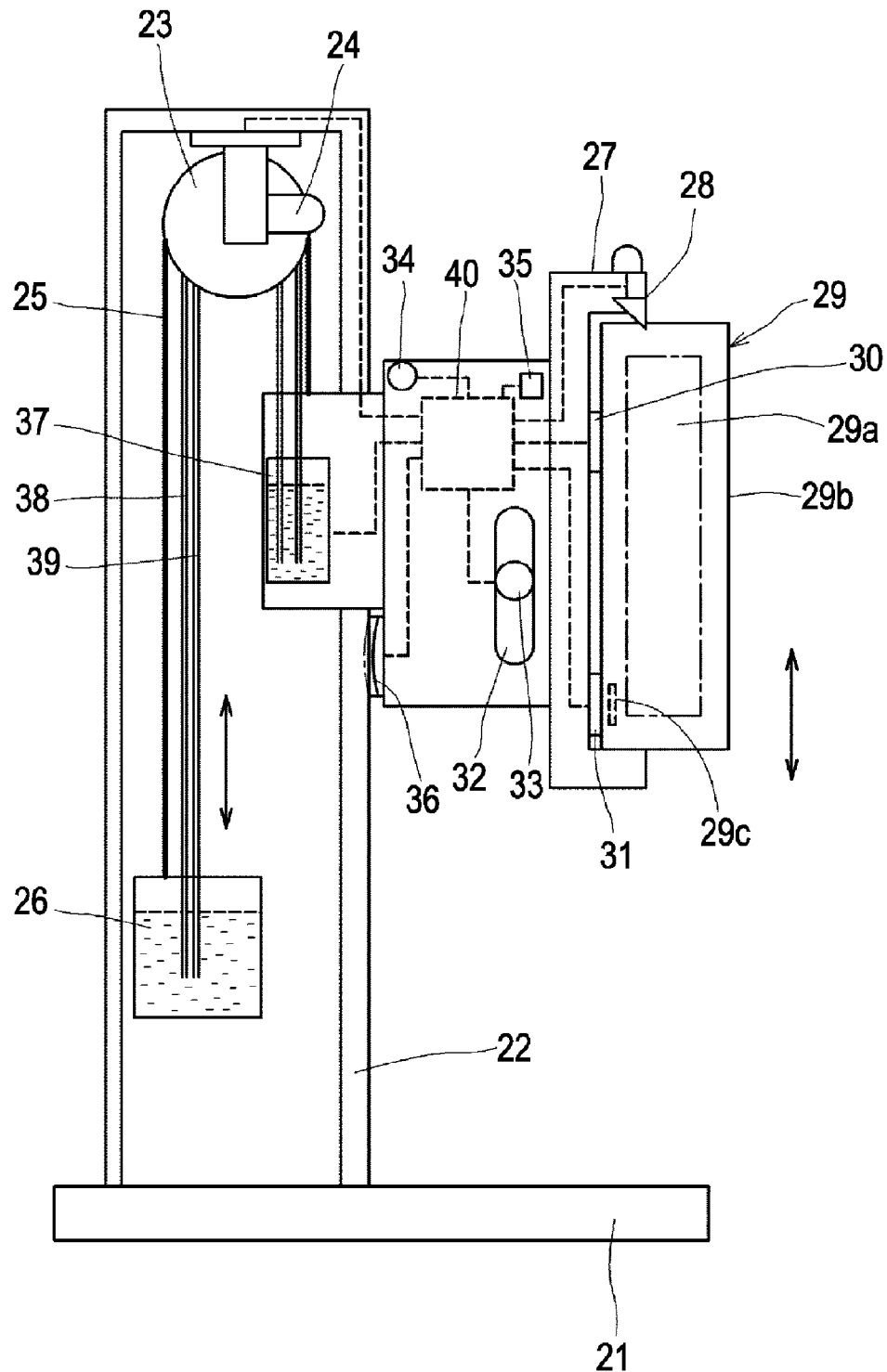
FIG. 1 is a configuration diagram of a medical imaging apparatus according to a first embodiment.

FIG. 1 is a configuration diagram showing a medical imaging apparatus with a vertical stand according to a first embodiment. A hollow column 22 is vertically provided on a pedestal 21. A pulley 23 is hung from an upper portion of the column 22. A safety lock portion 24 is attached to the pulley 23 to lock the pulley 23. A wire 25 is wound on the pulley 23. A first end of the wire 25 is connected to a weight 26, and a second end is connected to a holder 27, which is attached vertically movably along the column 22.

An imaging portion 29, which is one selected from a plurality of types of imaging portions for detecting two-dimensional images of subjects, is detachably attached to a front surface of the holder 27 via a detachment/attachment lock portion 28 driven by means of an actuator. Each of the imaging portions 29 includes a detector 29a, a housing 29b that covers the detector 29a, and a built-in identification plate 29c.

Also, a device attachment detecting unit 30 that detects whether the imaging portion 29 is attached or not, and a type detecting unit 31 that discriminates the type of the imaging portion 29, are provided between the imaging portion 29 and the holder 27. A movement lock switch 33 that has a handle 32 for an operation of vertical movement of the holder 27, a safety switch 34 that is operated when the imaging portion 29 is detached, and a detachment/attachment lock release button 35 are provided in a side surface of the holder 27. Also, a movement lock portion 36 that locks the holder 27 to the column 22 is provided on a surface of the holder 27 adjacent to the column 22.

Further, a weight adjusting portion 37 that stores liquid is provided in the holder 27. First ends of flexible pipes 38 and 39 are connected to the weight adjusting portion 37. The pipes 38 and 39 extend via the pulley 23, and second ends thereof communicate with liquid stored in the weight 26. The weight 26 containing the liquid has a weight which is balanced with the total weight of the holder 27 and the imaging portion 29. When the imaging portion 29 is to be moved, the imaging portion 29 is vertically movable as desired, with the weight balance constantly kept.

The holder 27 includes a controller 40 therein. The controller 40 is electrically connected to the detachment/attachment lock portion 28 of the pulley 23, the device attachment detecting unit 30, the type detecting unit 31, the movement lock switch 33, the safety switch 34, the detachment/attachment lock release button 35, and the weight adjusting portion 37.

When the controller 40 is operated, the controller 40 determines the weight and adjusts the weight balance, by discriminating the type of the imaging portion 29 with the type detecting unit 31, based on information of the identification plate 29c provided in the imaging portion 29. In particular, the liquid stored in the weight adjusting portion 37 moves between the weight adjusting portion 37 and the inside of the weight 26 by way of a driven pump (not shown) through the pipes 38 and 39. Hence, the weight 26 is adjusted to provide a suitable weight balance even when the weight of the imaging portion 29 changes depending on the type thereof.

When the detachment/attachment lock release button 35 is operated, detachment or attachment inhibition of the imaging portion 29 with the detachment/attachment lock portion 28 is eliminated. Thus, the imaging portion 29 becomes detachable from the holder 27. While the inhibition is eliminated, the movement lock switch 33 is nonfunctional even when the movement lock switch 33 is operated.

Figure 2:
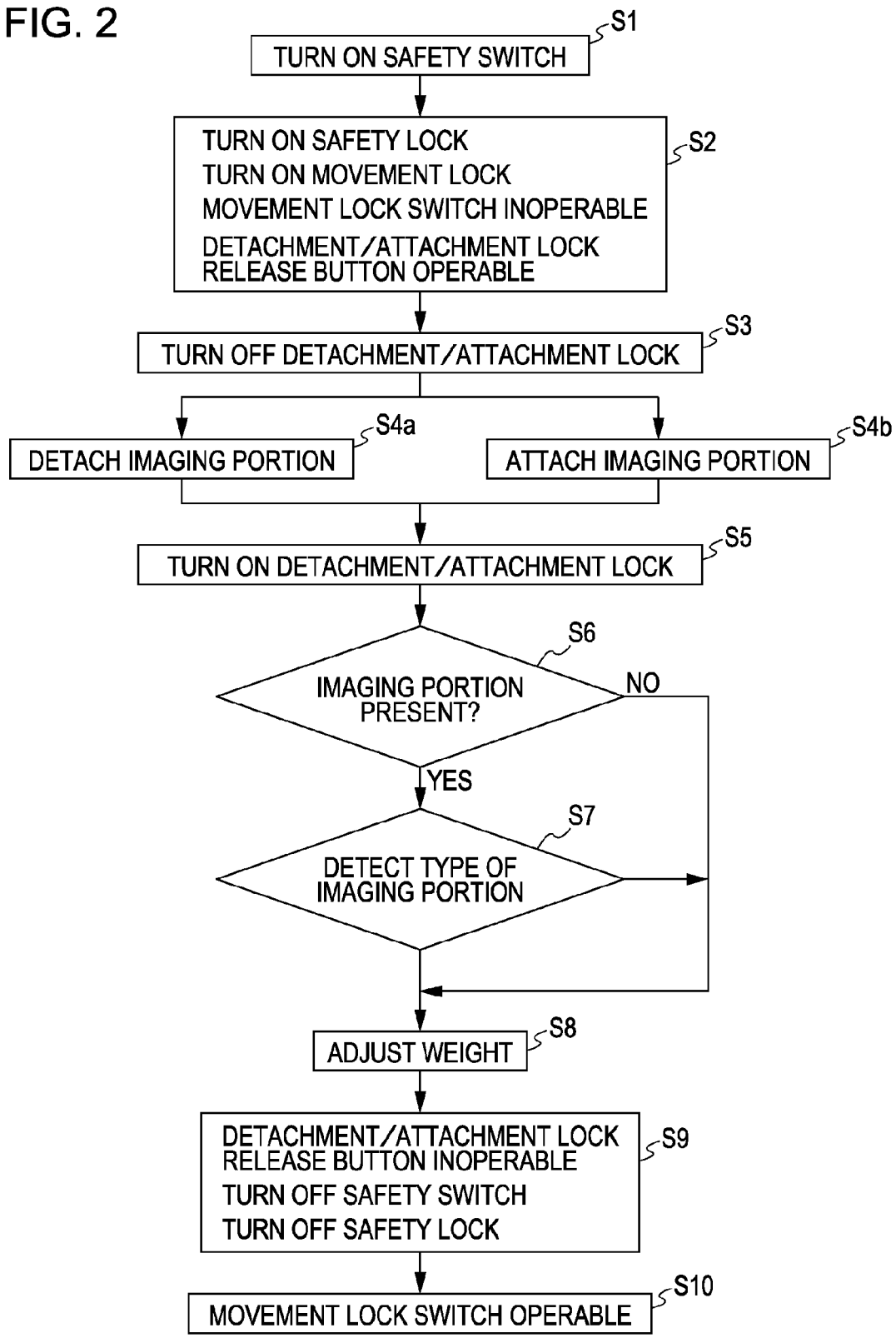
FIG. 2 is a flowchart showing an operation with a safety switch of the medical imaging apparatus.

FIG. 2 is a flowchart showing an operation with the safety switch 34. First, in step S1, when the safety switch 34 is turned ON, the procedure goes to step S2, in which the movement lock portion 36 and the safety lock portion 24 attached to the pulley 23 are locked. In addition, the movement lock switch 33 becomes inoperable, and the detachment/attachment lock release button 35 becomes operable.

Then, in step S3, the detachment/attachment lock portion 28 is released, and the procedure goes to step S4a or S4b, in which detachment (S4a) or attachment (S4b) of the imaging portion 29 becomes available. In step S5, the detachment/attachment lock portion 28 is turned ON, and the procedure goes to step S6, in which the device attachment detecting unit 30 detects the presence of the imaging portion 29. When it is determined that the imaging portion 29 is attached, the procedure goes to step S7, in which the type detecting unit 31 discriminates the type of the imaging portion 29. In step S8, weight adjustment is automatically performed so that the total weight of the imaging portion 29 with the type discriminated and the holder 27 is balanced with the weight of the weight 26. When it is determined that the imaging portion 29 is not attached in step S6, the procedure also goes to step S8, in which weight adjustment is automatically performed so that the holder 27 is balanced with the weight 26 similarly.

When the weight adjustment in step S8 is completed, the procedure goes to step S9, in which the safety switch 34 and the safety lock portion 24 are released. The detachment/attachment lock release button 35 becomes inoperable, and hence, a detachment operation is inhibited unless the safety switch 34 is released again. Finally, the procedure goes to step S10, in which the movement lock portion 36 becomes operable. Thus, the operation for vertical movement of the holder 27 becomes available.

With such an automatic control unit, which works in association with the detection of the type of the imaging portion 29, the burden on the operator is reduced, the likelihood of errors in operation is reduced, and the imaging portion 29 can be easily detached or attached.

Second Embodiment

Figure 3:
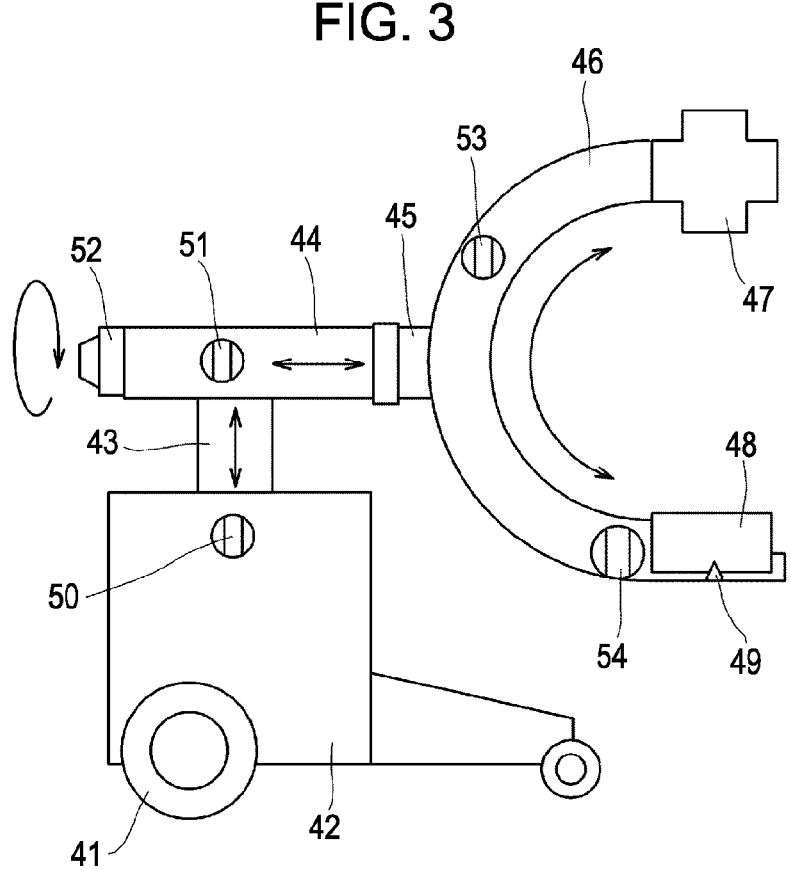
FIG. 3 is a configuration diagram of a medical imaging apparatus according to a second embodiment.

FIG. 3 is a configuration diagram showing a medical imaging apparatus which uses a movable C-arm according to a second embodiment. A main body 42 has wheels 41. A column 43, vertical movement of which is adjustable, is vertically provided on the main body 42. A horizontal supporting portion 44, front-rear movement of which is adjustable, is attached on the column 43. A C-arm 46 is provided at the horizontal supporting portion 44 with a C-arm holder 45 interposed therebetween. The C-arm 46 is slidable in a direction indicated by an arrow along the shape of the C-arm 46. A radiation source 47 and an imaging portion 48 are attached to both ends of the C-arm 46 to face each other. In addition, an imaging portion detecting unit 49 that detects the presence and type of the imaging portion 48 is provided between the C-arm 46 and the imaging portion 48.

A lever 50 for vertically moving the column 43 is provided in a side surface of the main body 42. A lever 51 for moving the horizontal supporting portion 44 forward and rearward is provided in a side surface of the horizontal supporting portion 44. Also, a lever 52 for rotating the horizontal supporting portion 44 is provided at an end portion of the horizontal supporting portion 44. Further, a lever 53 for slidably rotating the C-arm 46 is provided in a side surface of the C-arm 46. A detachment/attachment lock lever 54 for allowing the imaging portion 48 to be detached or attached is provided at the C-arm 46.

The imaging portion 48 is detachable from and attachable to the C-arm 46. For example, the type of the imaging portion 48 can be changed depending on the purpose of use, or the imaging portion 48 can be left detached and the medical imaging apparatus can be used as a movable radiation source. The detachment/attachment lock lever 54 is not released unless operations of all the levers 50, 51, 52, and 53 are suspended.

Figure 4:
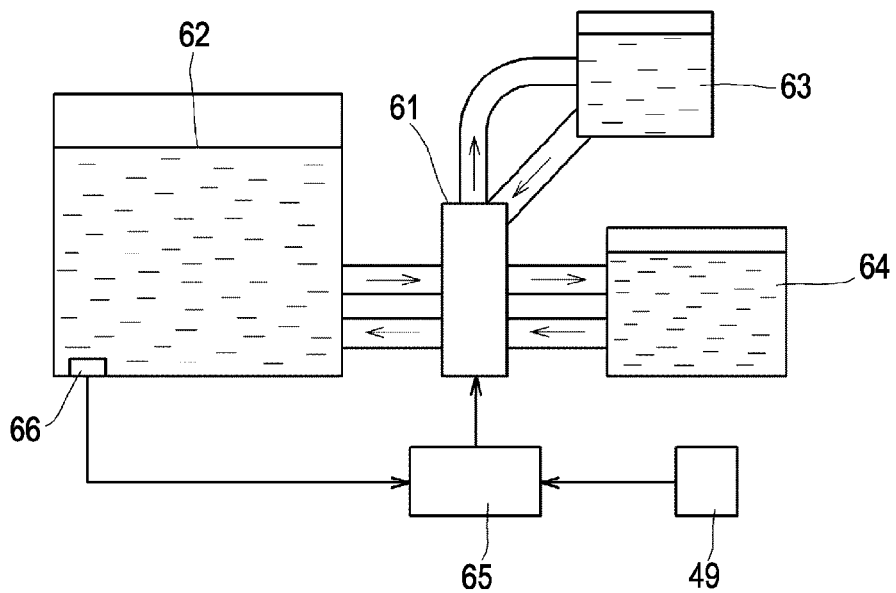
FIG. 4 is a configuration diagram of a weight adjustment mechanism according to the second embodiment.

FIG. 4 shows an example of a weight adjustment mechanism according to the second embodiment. A pump 61 is connected to a supply tank 62 provided inside the main body 42, a cooling portion 63 attached to the radiation source 47, and a weight adjustment tank 64 attached to the C-arm 46 provided near the imaging portion 48. Also, the pump 61 is connected to a controller 65. The controller 65 is connected to the imaging portion detecting unit 49 of the imaging portion 48, and a residual quantity detecting unit 66 that detects a residual quantity of liquid provided in the supply tank 62.

During normal use, in the weight adjustment mechanism, the cooling portion 63 cools the radiation source 47. However, when the imaging portion 48 is detached or attached, the controller 65 that has received a signal from the imaging portion detecting unit 49 of the imaging portion 48 controls the pump 61 based on a signal from the residual quantity detecting unit 66 of the supply tank 62, and adjusts the liquid quantity in the weight adjustment tank 64, to control the weight balance of the apparatus. The operations of the levers are fixed and the levers are kept inoperable until the adjustment of the weight balance is completed.

With such a control unit, a possibility of performing a detachment or attachment operation of the imaging portion 48 while the movable portions are unlocked is reduced, and the detachment or attachment operation of the imaging portion 48 can be easily performed. Through a manual or automatic operation, the respective movement operations can be individually fixed or released.

Third Embodiment

Figure 5:
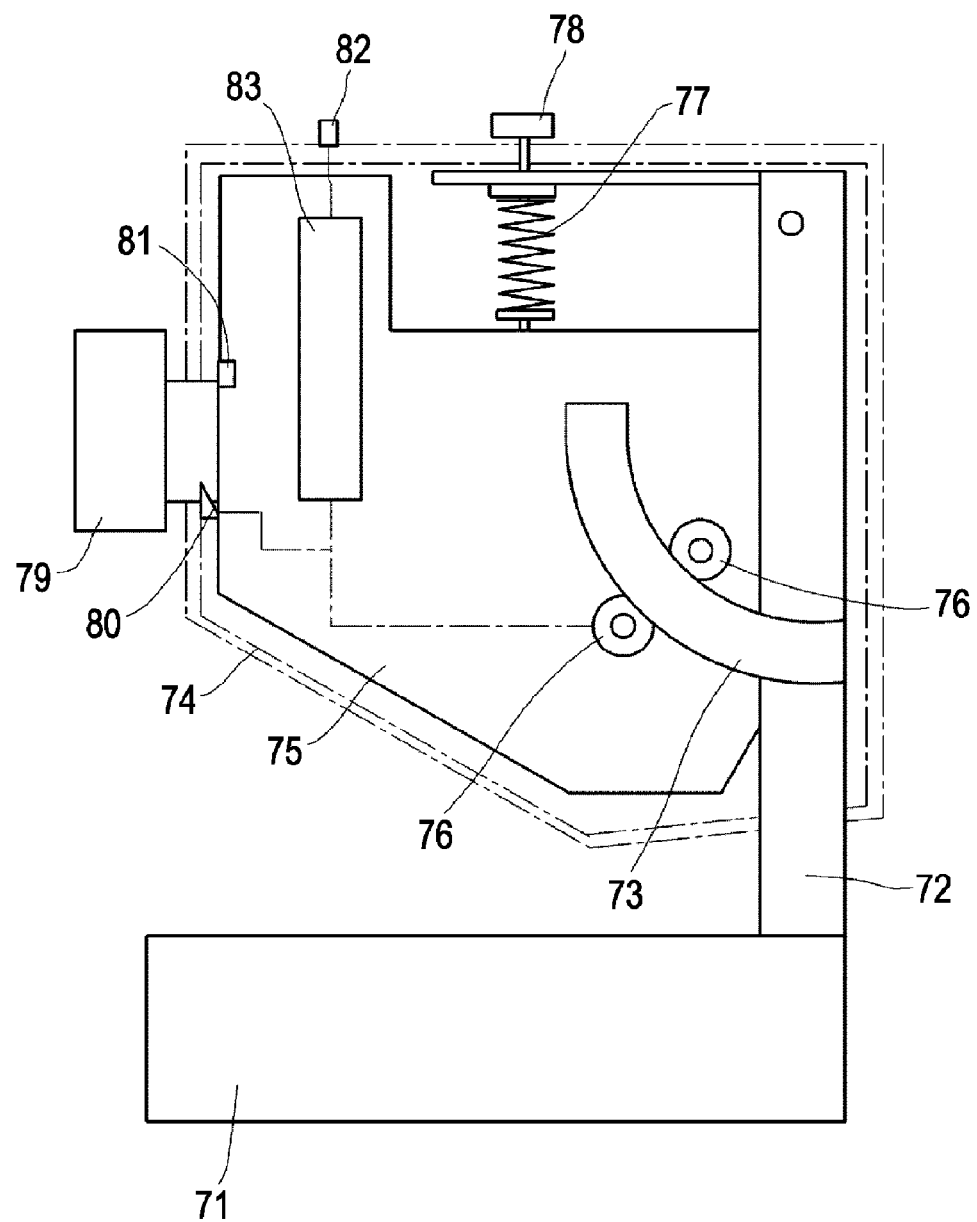
FIG. 5 is a configuration diagram of a medical imaging apparatus according to a third embodiment.
Figure 6:
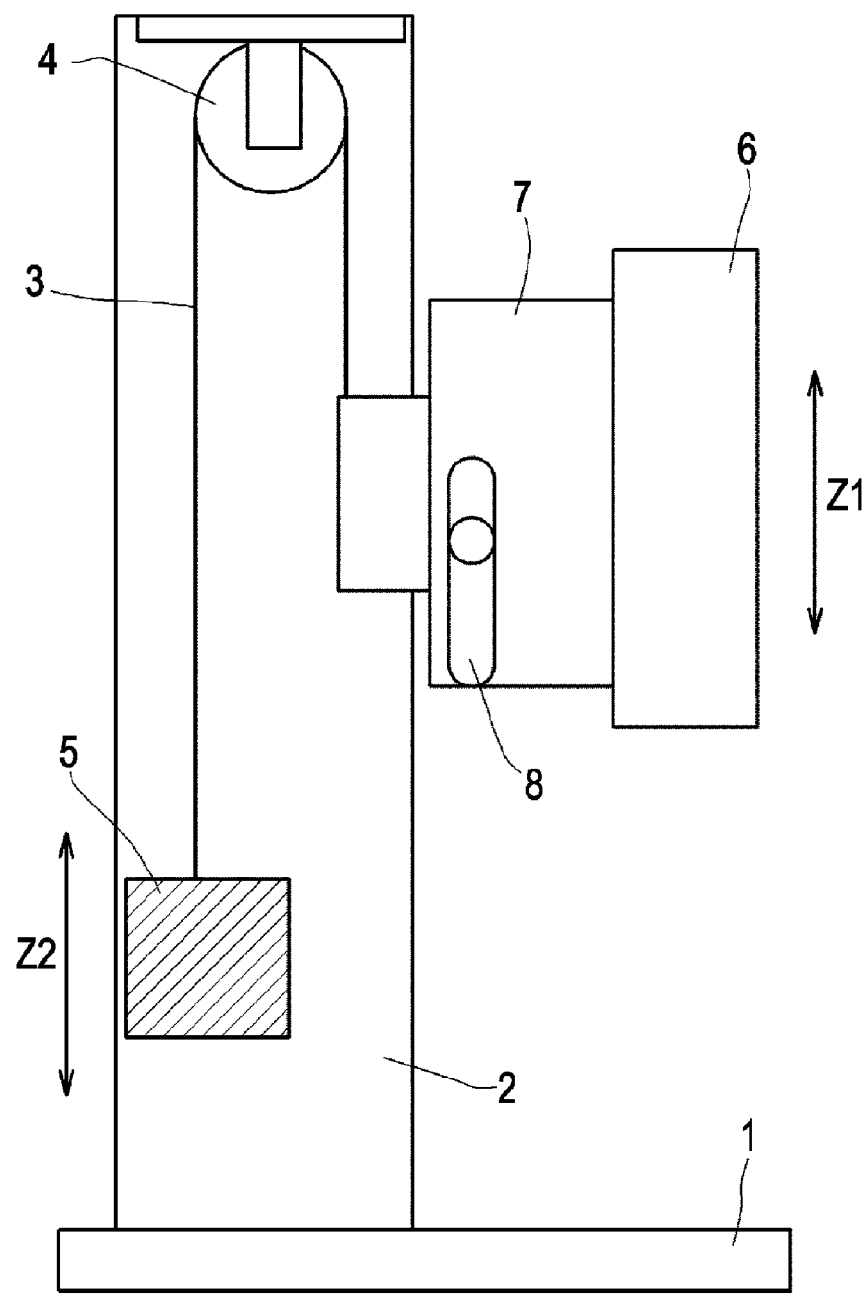
FIG. 6 is a configuration diagram showing a supporting base of a radiographic imaging apparatus according to a related art example.
Figure 7:
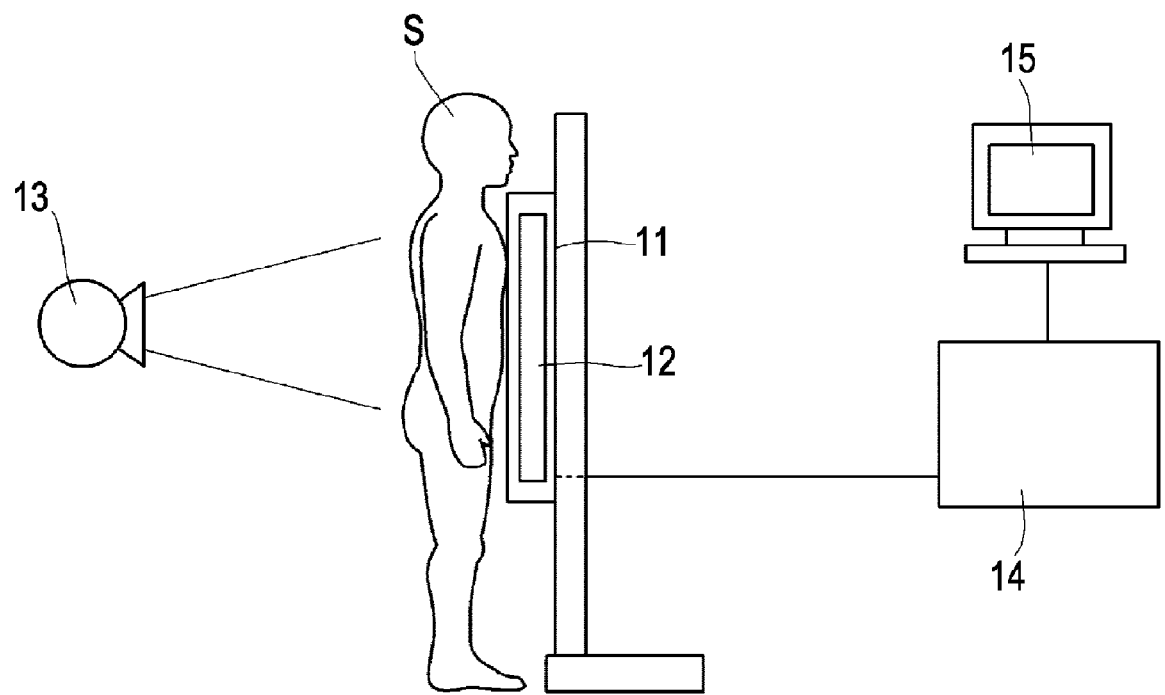
FIG. 7 is a configuration diagram of a radiographic imaging apparatus according to a related art example.

FIG. 5 is a configuration diagram showing a fundus photography apparatus of a medical imaging apparatus according to a third embodiment. A column 72 is vertically provided on a pedestal 71. A head unit 74 is held with a circular tilt arm 73 attached to the column 72. An optical base 75 is arranged in the head unit 74. The head unit 74 is movable along a curved surface of the tilt arm 73 while using a pair of guide rollers 76 as guides.

A weight adjustment spring mechanism 77 is provided in an upper portion of the head unit 74. An adjustment dial 78 is provided to adjust a spring force of the weight adjustment spring mechanism 77. The head unit 74 is configured to be movable while the weight balance is constantly kept. The weight adjustment is performed such that the head unit 74 is stopped at a desired position even when the head unit 74 is manually moved.

An imaging portion 79 is attached to a front surface of the head unit 74. A camera lock portion 80 inhibits the imaging portion 79 from being detached or attached. A type detecting unit 81 detects the type of the imaging portion 79. A lock button 82 is provided on an upper surface of the head unit 74. The lock button 82 is connected to a controller 83 provided inside the head unit 74. The camera lock portion 80 is configured to be released when the guide rollers 76 are fixed and the head unit 74 is held in its current tilt position. The imaging portion 79 is not detached unless the tilt movement is being locked.

Also, the weight adjustment spring mechanism 77 and the type detecting unit 81 are connected to the controller 83. The lock button 82 is not released unless a value of the weight adjustment spring mechanism 77 meets a value preset for each type of the imaging portion 79. With such a control unit, the possibility that balance may be disrupted due to a detachment or attachment operation and tilt movement is unintentionally operated, is reduced, and the imaging portion 79 cam be safely detached or attached.

As many apparently widely different embodiments of the present invention can be made without departing from the spirit and scope thereof, it is to be understood that the invention is not limited to the specific embodiments thereof except as defined in the claims.

This application claims the benefit of Japanese Application No. 2007-207881, filed Aug. 9, 2007, which is hereby incorporated by reference herein in its entirety.

What is claimed is:

1. A medical imaging apparatus comprising:
    an imaging unit configured to detect or capture a two-dimensional image of a subject;
    a holding unit configured to detachably hold the imaging unit;
    a moving unit configured to change a position of the imaging unit manually;
    a balance control unit configured to keep a weight balance when the imaging unit is moved;
    a fixing unit configured to inhibit the moving unit from being operated; and
    a detachment/attachment inhibiting unit configured to inhibit the imaging unit from being detached or attached when the fixing unit is being unlocked.

2. The medical imaging apparatus according to claim 1, further comprising a detecting unit configured to determine a type or/and presence of the imaging unit.

3. The medical imaging apparatus according to claim 2,
    wherein any one type selected from a plurality of types of imaging unit with different weights is attachable to the holding unit, and
    wherein the balance control unit is configured to adjust the weight balance in accordance with the type or/and the presence of the imaging unit determined by the detecting unit.

4. The medical imaging apparatus according to claim 3, wherein the fixing unit is controlled so as not to be unlocked when the weight balance is not adjusted.

* * * * *